United States Patent [19]

Ohsumi et al.

[11] Patent Number: 5,698,229
[45] Date of Patent: *Dec. 16, 1997

[54] ANTIMICROBIAL COMPOSITION

[75] Inventors: Shuichi Ohsumi, Osaka; Hideki Kato, Kuwana, both of Japan

[73] Assignee: Toagosei Co., Ltd., Tokyo, Japan

[*] Notice: The term of this patent shall not extend beyond the expiration date of Pat. No. 5,405,644.

[21] Appl. No.: 81,126

[22] Filed: Jun. 25, 1993

[30] Foreign Application Priority Data

Jun. 30, 1992 [JP] Japan .................. 4-196062
Jul. 24, 1992 [JP] Japan .................. 4-217474

[51] Int. Cl.$^6$ .......... A01N 59/00; A01N 59/06; A01N 59/16; A01N 59/26; A01N 43/647; C09D 5/14

[52] U.S. Cl. .......... 424/604; 424/405; 424/409; 424/421; 424/600; 424/601; 424/602; 424/605; 424/606; 424/617; 424/618; 424/619; 514/359; 514/972; 106/15.05; 106/18.31; 502/60; 523/122; 548/257

[58] Field of Search .................. 424/618, 617, 424/601, 602, 604, 606, 619, 405, 409, 421, 600, 605; 548/257; 514/359, 972; 523/122; 106/15.05, 18.31; 502/60

[56] References Cited

U.S. PATENT DOCUMENTS

| | | | |
|---|---|---|---|
| 3,988,647 | 10/1976 | Bolon et al. | 361/779 |
| 4,933,178 | 6/1990 | Capelli | 424/617 |
| 4,938,955 | 7/1990 | Niira et al. | 424/618 |
| 5,405,644 | 4/1995 | Ohsumi et al. | 427/2.31 |

FOREIGN PATENT DOCUMENTS

| | | |
|---|---|---|
| 288063 | 10/1988 | European Pat. Off. . |
| 48-26012 | 8/1973 | Japan . |
| 60-159191 | 8/1985 | Japan . |
| 3193701 | 8/1993 | Japan . |
| 2238044 | 5/1991 | United Kingdom . |

OTHER PUBLICATIONS

WPIDS Abstract, Accession No. 85–240877; abstracting JP 60–159191 (1985).

The Merck Index, 10th ed., Merck & Co., Inc., NJ, 1983, p. 1223, item No. 8360.

Derwent Abstract Accession No. 91–146140, abstracting JP 3–83905, Apr. 1991.

Derwent Abstract Accession No. 91–146141, abstracting JP 3–83906, Apr. 1991.

*Primary Examiner*—John Pak
*Attorney, Agent, or Firm*—Browdy and Neimark

[57] ABSTRACT

An antimicrobial composition, characterized by containing an inorganic compound on which silver ion is supported and a compound represented by the following formula [2]:

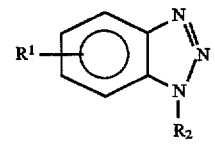

wherein $R^1$ is hydrogen or a lower alkyl group and $R^2$ is hydrogen or an alkali metal.

9 Claims, No Drawings

ANTIMICROBIAL COMPOSITION

FIELD OF INVENTION

The present invention relates to preventing undesired discoloration of various compositions containing, as a microbicide, an inorganic compound having silver ion supported thereon, said discoloration being caused by the silver ion.

Accordingly, by the use of particular compounds, the present invention imparts antibacterial or antifungal activity to coating compositions used as paints or surface treating agents to be coated on the surface of architectural structures such as exterior walls and interior walls, building materials such as decorative sheets, fibers, various resin molded articles, paper products or the like, and furthermore to compositions such as sealing materials, fillers and impregnating agents, and simultaneously prevents unexpected discoloration caused by silver ion used for imparting the antibacterial or antifungal activity.

BACKGROUND OF INVENTION

A number of microbicides capable of exhibiting antibacterial activity when contained in coating compositions, resin moldings, papers and binders, have been proposed. Among them, inorganic microbicides have recently been noticed to be excellent in durability.

Most of the inorganic microbicides are inorganic compounds on which silver ions are supported by various methods to exhibit antimicrobial activity and the inorganic compounds on which silver ions are to be supported include, for example, active carbon, apatite, zeolite, and various phosphates.

However, compositions containing the inorganic microbicides on which silver ion is supported (hereinafter referred to as merely "microbicides") suffer from the problem that they tend to discolor into a color which would not be expected from the starting color of the compositions and the color of the microbicides (for example, liver brown or coffee color), because the silver ion dissolves away in a slight amount. That is, when various compositions are prepared by mixing a microbicide with a resin or the like, if a liquid substance such as a solvent is present in the resin, the silver ion supported on the microbicide readily dissolves away. Therefore, the compositions and products prepared therefrom tend to undergo discoloration, and this is conspicuous in coating compositions.

In application of the sealing materials, which are used for enhancing waterproofness or airtightness by filling them in gaps, they are often filled in the gaps without completely removing fungi or bacteria present in the gaps, and water contacting the sealed surface or water vapor in the air is apt to remain in the sealed portion. Therefore, with lapse of time after filling the sealing material, the surface of the sealed portion often becomes stained with discoloration due to generation of fungi or bacteria, such as seen in joints of tiles.

Moreover, in many cases, sealing materials are used in such a manner that they are allowed to be in contact with water for a long period of time, and as especially conspicuous in the case of cement materials, many of the sealing materials are strongly alkaline, and sealing compositions prepared by mixing a sealing material with a microbicide show especially marked tendency of discoloration. In addition, in some cases, substantially no antibacterial and antifungal effects are exhibited.

In an attempt to inhibit discoloration of resins caused by silver ion, it has been proposed to use various stabilizers in combination with the antimicrobial compositions. For example, various stabilizers such as benzotriazole compounds, oxalic acid anilide compounds, salicylic acid compounds, hindered amine compounds and hindered phenol compounds have been known as additives to antimicrobial resin compositions comprising a resin and an antimicrobial zeolite having silver ion supported thereon. (cf. Japanese Patent Kokai No. 63-265958).

Although various stabilizers used for inhibiting discoloration of compositions to which a microbicide is added have been proposed as mentioned above, the discoloration cannot be sufficiently inhibited by use of these stabilizers, and further improvement has been demanded.

SUMMARY OF INVENTION

An object of the present invention is to provide a method for preventing discoloration of antimicrobial compositions containing a microbicide, said discoloration being caused by silver ion, while maintaining excellent antimicrobial activity.

The inventors have conducted intensive research in an attempt to solve the above problems and have found that it is very effective to incorporate a discoloration inhibitor consisting of a specific compound in a composition to which a microbicide having silver ion supported thereon has been added. Thus, the present invention has been accomplished.

That is, the present invention relates to an antimicrobial composition, characterized by containing an inorganic compound on which silver ion is supported and a compound represented by the following formula [2]:

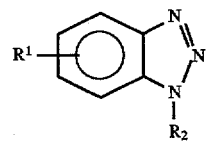

wherein $R^1$ is hydrogen or a lower alkyl group and $R^2$ is hydrogen or an alkali metal.

The present invention is explained in detail below.

DETAILED DESCRIPTION OF EMBODIMENTS

Principal Ingredient:

In the present invention, the term "composition" means compositions used for coating materials, sealing materials, fillers, impregnating agents, sealants and the like, and principal ingredients of these compositions include inorganic materials, organic materials and mixtures of inorganic and organic materials.

The inorganic materials include cement materials, metal oxide sols and others. The organic materials include natural resins, semisynthetic resins and synthetic resins, which may be either thermoplastic resins or thermosetting resins and may be in the form of solid, liquid or emulsion.

The cement materials are inorganic materials which are curable upon being mixed with water and mainly composed of calcium silicate, calcium aluminate, calcium sulfate, calcium oxide or the like.

Preferred examples of the cements are dolomite plaster, calcium hydroxide, plaster, gypsum, magensia cement, hydraulic lime, Roman cement, natural cement, Portland cement, alumina cement, lime-mixed cement, mixed Portland cement, water glass cement and dental cement.

These cements can be used as a cement paste prepared by kneading with water or can also be used as a cement mortar or a concrete prepared by kneading a blend of cement and aggregate such as sand with water. These can be used for laying bricks or building stones and setting roof tiles or floor tiles and can also be used as a main component of joint fillers.

The metal oxide sol is a particulate material produced by hydrolysis of an organometallic compound and has characteristics of forming a polymer by polycondensation in the presence of an acid or alkali catalyst. Preferable examples of the organometallic compound are alkoxides or acetoacetonates of tetravalent metals such as silicon, titanium and zirconium. In general, the metal oxide sol is readily subjected to polycondensation. Therefore, it is preferred to use a dispersion thereof in a solvent such as alcohol.

The resins may be either plastics or rubbers. Examples of the plastics are polyethylene, polypropylene, polyvinyl chloride, ABS resin, nylon, polyester, polyvinylidene chloride, polyamide, polystyrene, polyacetal, polycarbonate, acrylic resin, fluorocarbon resin, polyurethane elastomer, polyester elastomer, melamine resin, urea resin, tetrafluoroethylene resin, unsaturated polyester resin, epoxy resin, urethane resin and phenolic resin, and examples of the rubbers are natural rubber, and synthetic rubbers such as silicone rubber, SBR (styrene-butadiene rubber), CR (chloroprene rubber), EPM (ethylene-propylene rubber), FKM (fluorocarbon rubber), NBR (nitrile-butadiene rubber), CSM (chlorosulfonated polyethylene rubber), BR (butadiene rubber), IR (isoprene rubber), IIR (butyl rubber), urethane rubber and acrylic rubber.

As the principal ingredient of the coating materials, there may also be used resins containing in the molecule a functional group having photopolymerizability such as acryloyl group. Examples of these resins are polyol polyacrylate, polyester polyacrylate, polyepoxy polyacrylate and polyurethane acrylate.

The composition of the present invention may contain a solvent or a dispersant for dissolving or dispersing the resin when the above-mentioned principal ingredient is solid or highly viscous at room temperature.

The solvent or dispersant may be hydrophilic or oleophilic and their examples are as follows.

That is, examples of the hydrophilic solvent or dispersant are water, alcohols such as methyl alcohol, ethyl alcohol, ethylene glycol and glycerin, ketones such as acetone, and cellosolves. Examples of the oleophilic solvent or dispersant are aliphatic hydrocarbons such as hexane and cyclopentane and aromatic hydrocarbons such as benzene, toluene, xylene and petroleum ethers.

The solvent further includes plasticizing solvents such as dimethyl phthalate, diethyl phthalate, butylbenzene phthalate, dioctyl phthalate, diisooctyl phthalate, dicapryl phthalate, diisobutyl adipate, dioctyl adipate, dibenzyl sebacate, triphenyl phosphate, trioctyl phosphate, chlorinated paraffin, castor oil and camphor.

Among these solvents or dispersants, preferred are those which have characteristics to dissolve the discoloration inhibitor of the present invention, and typical examples thereof are methanol, ethylene glycol, methyl ethyl ketone, 10% aqueous sodium hydroxide solution, 2N-hydrochloric acid solution and water.

Microbicides:

The microbicides used in the present invention are unlimited as far as they are inorganic compounds on which silver ion is supported. Examples of the inorganic compounds on which silver ion is supported are shown below.

That is, the examples are inorganic adsorbents such as active carbon, active alumina and silica gel, and inorganic ion-exchangers such as zeolite, hydroxy apatite, zirconium phosphate, titanium phosphate, potassium titanate, hydrous antimony oxide, hydrous bismuth oxide, hydrous zirconium oxide and hydrotalcite.

The method for supporting silver ion on these inorganic compounds is unlimited and any of the known supporting methods can be employed. For example, there may be employed methods of physical or chemical adsorption, methods of ion-exchange reaction, methods of using a binder, methods of implanting a silver compound into an inorganic compound, and methods of forming a thin layer of a silver compound on the surface of an inorganic compound by thin film-forming processes such as vapor deposition, dissolution and precipitation reaction and sputtering.

Of these inorganic compounds, inorganic ion-exchangers are preferred because silver ion can be firmly supported thereon. Especially preferred microbicides are phosphates represented by the following formula [1].

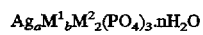

$$Ag_aM^1{}_bM^2{}_2(PO_4)_3 \cdot nH_2O \qquad [1]$$

wherein $M^1$ is at least one ion selected from alkali metal ion, alkaline earth metal ion, ammonium ion and hydrogen ion, $M^2$ is a tetravalent metal such as Ti, Zr, Sn or the like, n is a number which satisfies $0 \leq n \leq 6$, and a and b are positive numbers which satisfy $a+mb=1$ where m is a valence of $M^1$.

As the tetravalent metal Zr is preferable.

These antimicrobial compounds are crystalline compounds belonging to the space group R3c in which the constituting ions form a three-dimensional network structure.

Examples of the phosphates represented by the above formula [1] are shown below.

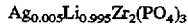

$Ag_{0.005}Li_{0.995}Zr_2(PO_4)_3$

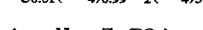

$Ag_{0.01}(NH_4)_{0.99}Zr_2(PO_4)_3$

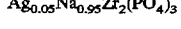

$Ag_{0.05}Na_{0.95}Zr_2(PO_4)_3$

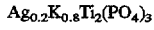

$Ag_{0.2}K_{0.8}Ti_2(PO_4)_3$

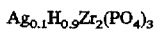

$Ag_{0.1}H_{0.9}Zr_2(PO_4)_3$

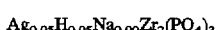

$Ag_{0.05}H_{0.05}Na_{0.90}Zr_2(PO_4)_3$

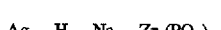

$Ag_{0.05}H_{0.55}Na_{0.40}Zr_2(PO_4)_3$

When the microbicide consisting of the phosphate represented by the above formula [1] is incorporated into resins using no or only a slight amount of a liquid substance such as a solvent, namely, by the so-called dry method, no discoloration of the resin compositions and the molded articles obtained therefrom occurs even if they are allowed to come into contact with a liquid. When the discoloration inhibitor of the present invention is additionally used, the discoloration inhibitor substantially prevents discoloration of the coating compositions containing a liquid coating base or a solvent and of the film obtained from the coating compositions. Thus, in this latter case, the above microbicides are especially excellent, and sealing compositions and the sealings obtained therefrom show substantially no discoloration when the compositions contain the discoloration inhibitor of the present invention in addition to the above microbicide. Therefore, also in this point the above microbicide is particularly excellent.

These phosphates can be prepared by firing process, wet process, hydrothermal process or the like. For example, they can be easily prepared by the wet process in the following manner.

Oxalic acid is added to an aqueous solution of zirconium oxynitrate and sodium nitrate with stirring and then phosphoric acid is further added. The reaction mixture is adjusted to pH 3.5 with an aqueous sodium hydroxide solution and refluxed with heating for 78 hours. The precipitate is subjected to filtration, washing with water, drying and grinding to obtain zirconium phosphate [$NaZr_2(PO_4)_3$] having a network structure. The product is immersed in an aqueous solution containing silver ion at a suitable concentration to obtain the compound represented by the formula [1].

In order to exhibit antifungal, antibacterial and antialgal activities, larger value a in the formula [1] is preferred, but when the value a is 0.001 or more, antifungal, antibacterial and antialgal activities can be sufficiently exhibited. However, in consideration of the fact that when the value a is less than 0.01, it may become difficult to exhibit antifungal, antibacterial and antialgal activities for a long period of time, and furthermore from the economical view point, the value a is preferably in the range of 0.01 to 0.5.

The content of the microbicide is preferably in the range of 0.05 to 50 parts by weight (hereinafter referred to as merely "parts") based on 100 parts (solid content) in total of the principal ingredient and other additives excluding the discoloration inhibitor, and more preferably in the range of 0.5 to 10 parts in consideration of antimicrobial activity and the economical efficiency.

Discoloration Inhibitors:

The discoloration inhibitor of the present invention is a compound represented by the following formula [2]:

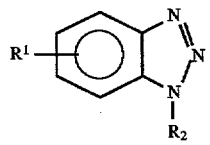

[2]

wherein $R^1$ is hydrogen, or a lower alkyl group and $R^2$ is hydrogen, or an alkali metal salt thereof.

Examples of the lower alkyl group are methyl, ethyl, n-propyl, isopropyl and butyl groups, and among them the methyl group is especially preferred in view of high stability of the compounds.

$R^2$ in the formula [2] is hydrogen or an alkali metal, and examples of the alkali metal are lithium, sodium, potassium and cesium.

Preferred examples of the compound represented by the above formula [2] are methylbenzotriazole and the potassium salt of methylbenzotriazole.

Benzotriazote compounds have been known as stabilizers for resins. However, according to the present invention it has been found that when the above-mentioned specific compound among the benzotriazole compounds is added to various compositions together with the microbicide, discoloration of various articles obtained from these compositions which is caused by silver ion can be highly inhibited. This fact is markedly surprising.

The amount of the discoloration inhibitor is preferably 0.1 to 100 parts, more preferably 1 to 10 parts based on 100 parts of the microbicide. If the amount is less than 0.1 part, there is a possibility that the discoloration cannot be sufficiently inhibited, and even if it is more than 100 parts, inhibition of discoloration no longer increases and rather it becomes difficult to exhibit characteristics required for the compositions, since the amount of the principal ingredient in the compositions decreases.

Other Ingredients:

In the present invention, as far as the effects to be obtained are not damaged, there may be optionally added the conventional colorants, moisture-proofing agents, waterproofing agents, ultraviolet absorbers, antioxidants, antifoaming agents, surfactants, foaming agents, fillers, extenders, flocculants, flame retardants and the like.

Process of Preparation:

The antimicrobial composition of the present invention can be easily prepared by mixing, incorporating or kneading the above various ingredients at a suitable temperature and pressure depending on characteristics of the principal ingredient used and on the object, and the actual operations may be conducted by conventional methods.

In order to efficiently inhibit the discoloration, it is preferred to previously add the discoloration inhibitor to the principal ingredient before adding the microbicide.

Method for Use:

The composition of the present invention is used by customary methods depending on the object and the use is not limited by the joint use with the microbicide or the discoloration inhibitor.

As for the usage of the composition, for example, in the case of coating composition, the known coating methods can be suitably employed depending on the kinds of the coating base and the material to be coated.

Specifically, there are such coating methods as brushing, padding, spraying, hot-spraying, airless spraying, electrostatic coating, roller coating, curtain flow coating, flow coating, dip coating, electro-deposition, tumbling, blade coating, spatula coating, centrifugal coating, die coating and the like. Furthermore, for forming a film on the surface of a material to be coated depending on the shape of the material, there are filling method to coat the surface of crevices and dents of the material to be coated, impregnating method to coat the surface of inter-communicating pores in the material to be coated or coat the outer surface of the material to be coated, and sealing method to coat the whole outer surface of the material to isolate the material from the external atmosphere.

After coating the material by the above-mentioned various methods, the film formed is dried at room temperature or 50° to 130° C., whereby the film firmly adheres to the material to be coated and thus, a film having a practical mechanical strength can be easily produced.

When a resin having photocurability is used as the principal ingredient, the film can be formed in a short time by irradiating the coated portion with an active energy ray such as ultraviolet ray.

In the thus obtained antimicrobial composition, since the silver ion is chemically and physically very stably supported on the microbicide, even when a liquid substance such as various solvents or dispersing media is contained or even when the composition is used in the alkaline area, the composition and articles made therefrom show substantially no discoloration and have antifungal, antibacterial and antialgal activities for a prolonged period of time even under severe conditions.

Uses:

The composition of the present invention can be used without any hindrance depending on the objects. For example, the sealing compositions are effective in the field where formation of sealings having antifungal, antialgal and antibacterial activities and free from discoloration is required, such as exterior wall, bathroom, pool, toilet room, lavatory, road, pier, water tank, silo and operating room, and are especially effective as jointing materials for tiles. The coating compositions are especially effective in the field where formation of films having antifungal, antialgal and antibacterial activities and free from discoloration is required, for example, surface treatment of building materials such as exterior wall and decorative sheet; fibers; various resin molded articles such as bucket and pot; and paper. Specifically, there are uses of forming antimicrobial film on the surface of the following materials.

That is, wall paper, external cladding of houses, interior wall of hospitals, inner and outer materials of cupboard, plastic containers for foods, chopping board, refrigerators, medical equipments, various packaging materials, brushes, waterworks, fibrous products such as sheets, washcloths, hand towels and face masks, leather goods such as bags and shoes, and porous materials such as air filter and water filter.

Effects:

In the antimicrobial composition of the present invention, silver ion has excellent chemical and physical stability and causes substantially no discoloration of the composition and articles obtained therefrom even when allowed to contact with liquid substances such as solvents or dispersing media, and the composition and the articles have antifungal, antibacterial and antialgal activities for a long time even under severe conditions.

Furthermore, in the case of the coating compositions, since antimicrobial films can be formed on the surface of materials by various methods, the compositions are useful not only as paints, but also as materials capable of forming antimicrobial films free from discoloration irrespective of the shape and the object of use. Furthermore, the antimicrobial sealing compositions have excellent effect of showing substantially no discoloration even under contacting with water or alkaline substances for a long time.

The present invention is explained in more detail by the following examples.

REFERENTIAL EXAMPLE 1

An aqueous zirconium sulfate solution and an aqueous ammonium dihydrogenphosphate solution were mixed at a ratio of zirconium and phosphorus of 2:3 to produce a precipitate. Then, pH of the resulting slurry was adjusted to 2 with an aqueous sodium hydroxide solution, followed by heating at 150° C. for 24 hours in the hydrothermal state to obtain crystalline zirconium phosphate.

The resulting zirconium phosphate was added to an aqueous silver nitrate solution and stirred for 4 hours at room temperature, sufficiently washed with water, dried and ground to obtain a microbicide. The resulting microbicide was white powder of 0.47 μm in average particle size.

Separately, a commercially available zeolite was subjected to the same silver ion exchanging as above to prepare a microbicide. The microbicides thus obtained are shown in Table 1.

TABLE 1

| Kinds of microbicides | Molecular formulas |
| --- | --- |
| A | $Ag_{0.18}(NH_4)_{0.82}Zr_2(PO_4)_3$ |
| B | $0.03Ag_2O \cdot 0.9Na_2O \cdot Al_2O_3 \cdot 2SiO_2$ |

EXAMPLE 1

[Preparation of Antimicrobial Coating Composition]

Ten parts of a polyvinyl chloride paste, 6 parts of DOP, 0.5 part of the microbicide obtained in Referential Example 1 and 0.05 part of a discoloration inhibitor were uniformly mixed to obtain an antimicrobial coating composition. For comparison, a composition to which neither the microbicide nor the discoloration inhibitor was added, and a composition to which only the discoloration inhibitor was not added, were prepared in the same manner as above. The resulting antimicrobial coating compositions and comparative samples are shown in Table 2.

TABLE 2

| Sample No. | Discoloration inhibitors | | Kinds of microbicides |
| --- | --- | --- | --- |
| 1 | No | | No |
| 2 | No | | A |
| 3 | BTZ | *1 | A |
| 4 | CHIMASSORB 944 | *2 | A |
| 5 | TINUVIN 320 | *3 | A |

Notes)
*1: Methylbenzotriazole
*2: Trade name of hindred amine light stabilizer having the following structural formula manufactured by Ciba-Geigy Corp.

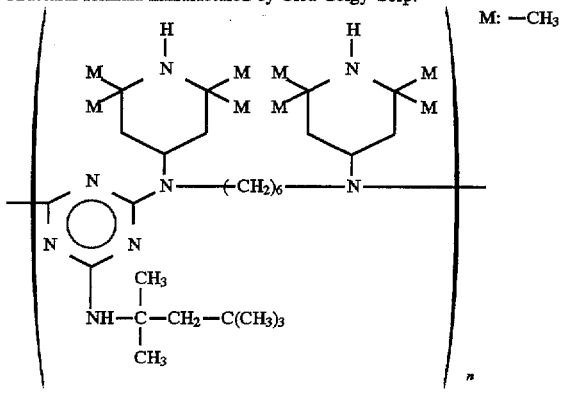

*3: Trade name of benzotriazole light stabilizer having the following structural formula manufactured by Ciba-Geigy Corp.

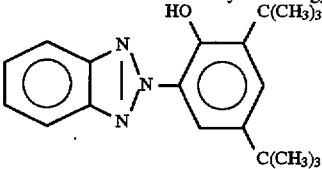

EXAMPLE 2

[Preparation of Antimicrobial Coating Composition]

Ten parts of a polyvinyl chloride paste, 6 parts of DOP, 0.5 part of the microbicide obtained in Referential Example 1, 0.05 part of a discoloration inhibitor, 0.25 part of a foaming agent (azodicarbonamide) and 0.25 part of a stabilizer (trade name FL44 manufactured by Asahi Denka Kogyo K.K.) were uniformly mixed to obtain an antimicrobial coating composition. For comparison, a composition to which neither the microbicide nor the discoloration inhibitor was added, and a composition to which only the discoloration inhibitor was not added, were prepared in the same manner as above. The resulting antimicrobial coating compositions and comparative samples are shown in Table 3.

TABLE 3

| Sample No. | Discoloration inhibitors | Kinds of microbicides |
|---|---|---|
| 6 | No | No |
| 7 | No | A |
| 8 | BTZ | A |
| 9 | CHIMASSORB 944 + BTZ | A |
| 10 | TINUVIN 320 + BTZ | A |

EXAMPLE 3

[Preparation of Antimicrobial Coating Composition]

Ten parts of an acrylic emulsion, 0.5 part of the microbicide obtained in Referential Example 1 and 0.05 part of a discoloration inhibitor were uniformly mixed to obtain an antimicrobial coating composition. For comparison, a composition to which neither the microbicide nor the discoloration inhibitor was added, and a composition to which the microbicide was added but the discoloration inhibitor was not added, were prepared in the same manner as above. The resulting antimicrobial coating compositions and comparative samples are shown in Table 4.

TABLE 4

| Sample No. | Discoloration inhibitors | Kinds of microbicides |
|---|---|---|
| 11 | No | No |
| 12 | No | A |
| 13 | BTZ (K) *4 | A |
| 14 | BTZ (K) + TINUVIN 320 | A |
| 15 | IRGANOX1010 *5 | A |
| 16 | TINUVIN 320 | A |
| 17 | CHIMASSORB 944 | A |
| 18 | IRGANOX MD1024 *6 | A |
| 19 | IRGAFOS 168 *7 | A |
| 20 | No | B |
| 21 | BTZ (K) *4 | B |

Notes)
*4: Potassium salt of methylbenzotriazole
*5: Trade name of hindered phenol light stabilizer having the following structural formula manufactured by Ciba-Geigy Corp.

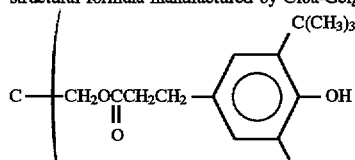

*6: Trade name of hydrazine type metal inactivating agent having the following structural formula manufactured by Ciba-Geigy Corp.

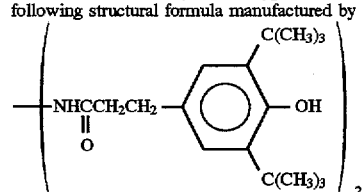

*7: Trade name of phosphorus type processing stabilizer having the following structural formula manufactured by Ciba-Geigy Corp.

TABLE 4-continued

| Sample No. | Discoloration inhibitors | Kinds of microbicides |
|---|---|---|

$$P\left[-O-\underset{C(CH_3)_3}{\underset{|}{\bigcirc}}-C(CH_3)_3\right]_3$$

Evaluation Test 1

[Weathering Test]

Each of the coating compositions of Sample Nos. 1–21 obtained in Examples 1–3 was uniformly coated on a white Kent paper. The thus coated papers were employed as test products (The test product prepared by coating the coating composition of "Sample No. n" is referred to as "Test product No. n"). Weathering resistance of the test products was measured using a forced deterioration tester UC-1 manufactured by Toyo Seiki Mfg. Co., Ltd. The exposing conditions of UC-1 were irradiation with ultraviolet rays (60° C.) and humidification (40° C.) which were repeated alternately every one hour and exposing time was 24 hours. The color (L, a, b) of the test product before and after the exposure was measured by a color-difference meter SZ-Σ80 manufactured by Nihon Denshoku Kogyo Co., Ltd. The results are shown in Tables 5, 6 and 7.

TABLE 5

| Test product No. | L | a | b |
|---|---|---|---|
| 1 | 82.0 | −0.8 | 3.1 |
| 2 | 44.5 | 11.4 | 15.6 |
| 3 | 73.9 | 4.4 | 6.2 |
| 4 | 62.6 | 4.8 | 17.4 |
| 5 | 38.0 | 12.8 | 14.3 |

As can be seen from Table 5, as compared with the white test product No. 1 containing only the coating base and containing neither the microbicide nor the discoloration inhibitor, the test product No. 2 containing only the microbicide and containing no discoloration inhibitor and the test product No. 5 containing the microbicide together with the conventional discoloration inhibitor disclored to liver brown, and the test product No. 4 containing the microbicide together with the conventional discoloration inhibitor disclored to yellowish brown. On the other hand, the test product No. 3 containing the microbicide together with methylbenzotriazole showed substantially no discoloration.

TABLE 6

| Test product No. | Before weathering test | | | After weathering test | | |
|---|---|---|---|---|---|---|
| | L | a | b | L | a | b |
| 6 | 71.4 | −4.3 | 33.5 | 76.8 | −1.4 | 29.4 |
| 7 | 22.4 | 10.9 | 5.3 | 24.4 | 8.7 | 5.2 |
| 8 | 73.3 | −2.2 | 32.8 | 65.0 | 4.6 | 28.9 |
| 9 | 73.3 | −1.4 | 33.1 | 60.0 | 8.1 | 26.3 |
| 10 | 77.0 | −3.7 | 33.4 | 71.1 | 0.7 | 26.3 |

As can be seen from Table 6, as compared with the white test product No. 6 containing the coating base, the foaming agent and the stabilizer but containing neither the microbicide nor the discoloration inhibitor, the test product No. 7 containing only the microbicide and containing no discoloration inhibitor in addition to the coating base, the foaming agent and the stabilizer already discolored to liver brown before the weathering test. On the other hand, the test product Nos. 8–10 containing methylbenzotriazole or this and the conventional discoloration inhibitor together with the microbicide showed substantially no discoloration before and after the weathering test.

TABLE 7

| Test product No. | Before weathering test | | | After weathering test | | | Color difference ΔE |
| --- | --- | --- | --- | --- | --- | --- | --- |
| | L | a | b | L | a | b | |
| 11 | 95.9 | −0.4 | 1.2 | 95.1 | −0.4 | 1.4 | 0.8 |
| 12 | 77.4 | 3.8 | 7.9 | 77.7 | 2.3 | 18.4 | 11.0 |
| 13 | 95.6 | −0.5 | 2.2 | 94.8 | −0.3 | 2.8 | 0.9 |
| 14 | 95.8 | −0.4 | 2.0 | 93.4 | −0.1 | 2.5 | 2.5 |
| 15 | 90.4 | 0.9 | 6.0 | 86.3 | 0.7 | 12.1 | 7.5 |
| 16 | 86.1 | 2.2 | 6.8 | 83.5 | 0.9 | 15.4 | 9.0 |
| 17 | 87.1 | 1.9 | 6.1 | 81.5 | 1.1 | 14.8 | 10.0 |
| 18 | 93.9 | 0.2 | 2.0 | 88.8 | 1.8 | 6.5 | 7.0 |
| 19 | 93.4 | 0.2 | 3.9 | 86.3 | 1.3 | 8.7 | 8.7 |
| 20 | 83.2 | 0.7 | 6.2 | 73.0 | 4.1 | 12.3 | 12.4 |
| 21 | 95.8 | −0.4 | 2.1 | 92.1 | 0.4 | 2.8 | 3.8 |

As can be seen from Table 7, as compared with the white test product No. 11 containing only the coating base and containing neither the microbicide nor the discoloration inhibitor, the test product Nos. 12 and 20 containing only the microbicide and containing no discoloration inhibitor in addition to the coating base already discolored to liver brown before the weathering test and more strongly discolored after the weathering test, and the test product Nos. 15–19 containing the conventional discoloration inhibitor together with the microbicide discolored to yellow before the weathering test and further discolored to yellowish brown after the weathering test. On the other hand, the test product Nos. 13, 14 and 21 containing potassium salt of methylbenzotriazole together with the microbicide showed substantially no discoloration before and after the weathering test.

Evaluation Test 2

[Antimicrobial Activity Test]

The coating compositions of the sample Nos. 1, 2 and 3 obtained in Example 1 were subjected to antimicrobial activity test in the following manner.

Each of the coating compositions was coated on a white Kent paper of 5 cm×5 cm to form a film of coating. This paper was used as a test paper. The surface thereof was uniformly inoculated with a bacteria solution of *Escherichia coli* as test bacteria so that the number of bacteria was $10^5$ per one white Kent paper and stored at 36° C. for 6 hours. Thereafter, the surviving bacteria on the test paper were washed out with a medium for measuring the number of bacteria (SCDLP liquid medium) and the washing solution was used as a test solution. The number of surviving bacteria in the test solution was measured by a dilution plate culture method (36° C., 2 days) with the medium for measuring the number of bacteria, and the number of surviving bacteria per one test paper was calculated therefrom. The results are shown in Table 8.

TABLE 8

| Sample No. | The number of bacteria |
| --- | --- |
| 1 | $2.5 \times 10^3$ |
| 2 | 0 |
| 3 | 0 |

As can be seen from Table 8, sample Nos. 2 and 3 containing the microbicide showed excellent antimicrobial activity.

Sample Nos. 8, 9, 10, 13, 19 and 21 containing the microbicide were subjected to the same antimicrobial activity test as above. The number of surviving bacteria was 0 for all samples. Thus, it was confirmed that the samples containing the microbicide all had sufficient antimicrobial activity.

EXAMPLE 4

[Preparation of Antimicrobial Sealing Composition]

100 parts of a sealing material (commercially available white cement), 1 part of the microbicide obtained in Referential Example 1 and 0.2 part of a discoloration inhibitor were mixed, and 80 parts of water was further added thereto, and these were uniformly mixed to obtain an antimicrobial sealing composition.

For comparison, a sealing composition containing neither the microbicide nor the discoloration inhibitor and sealing compositions which did not contain only the discoloration inhibitor Were prepared in the same manner as above. The thus obtained antimicrobial sealing compositions and comparative sealing compositions are shown in Table 9.

TABLE 9

| Sample No. | Discoloration inhibitors | Kinds of microbicides |
| --- | --- | --- |
| 22 | No | No |
| 23 | No | A |
| 24 | BTZ (K) | A |
| 25 | CHIMASSORB 944 | A |
| 26 | TINUVIN 320 | A |
| 27 | IRGANOX 1010 | A |
| 28 | No | B |
| 29 | BTZ (K) | B |

EXAMPLE 5

[Preparation of Antimicrobial Sealing Composition]

5 parts of the microbicide obtained in Referential Example 1, 100 parts of an aqueous acrylic resin sealing material (manufactured by Cemedain Co., Ltd.) and 0.5 part of a discoloration inhibitor were uniformly mixed to obtain an antimicrobial sealing composition.

For comparison, a sealing composition containing neither the microbicide nor the discoloration inhibitor and sealing compositions which did not contain only the discoloration inhibitor were prepared in the same manner as above. The thus obtained antimicrobial sealing compositions and comparative sealing compositions are shown in Table 10.

TABLE 10

| Sample No. | Discoloration inhibitors | Kinds of microbicides |
|---|---|---|
| 22 | No | No |
| 31 | No | A |
| 32 | BTZ (K) | A |
| 33 | CHIMASSORB 944 | A |
| 34 | TINUVIN 320 | A |
| 35 | IRGANOX 1010 | A |
| 36 | TINUVIN 320 + BTZ (K) | A |
| 37 | No | B |
| 38 | BTZ (K) | B |

Evaluation Test 3

[Weathering Test]

Each of the sealing compositions of sample Nos. 22–29 obtained in Example 4 was uniformly filled in a mold of 5 cm×5 cm×0.5 cm and air-dried for 1 day. Separately, each of the sealing compositions of sample Nos. 30–38 obtained in Example 5 was uniformly coated on a white Kent paper. These were used as test products, and weathering resistance thereof was measured in the same manner as the evaluation test 1. The results are shown in the following Tables 11 and 12.

TABLE 11

| Test product | Before weathering test | | | After weathering test | | |
|---|---|---|---|---|---|---|
| No. | L | a | b | L | a | b |
| 22 | 95.1 | −2.0 | 2.4 | 95.4 | −1.8 | 2.7 |
| 23 | 80.8 | 1.5 | 15 | 80.2 | 1.2 | 14 |
| 24 | 94.7 | −1.7 | 2.4 | 93.8 | −2.7 | 3.9 |
| 25 | 81.2 | 2.2 | 12 | 80.0 | 3.5 | 15 |
| 26 | 81.3 | 2.1 | 16 | 79.9 | 2.5 | 15 |
| 27 | 80.1 | 1.9 | 13 | 80.9 | 2.9 | 16 |
| 28 | 72.1 | 2.4 | 17 | 72.0 | 2.3 | 16 |
| 29 | 92.9 | −2.0 | 2.6 | 92.4 | −2.0 | 4.0 |

As can be seen from Table 11, as compared with the test product No. 22 containing only the sealing base and containing neither the microbicide nor the discoloration inhibitor, the test product Nos. 23 and 28 containing only the microbicide and containing no discoloration inhibitor and the test product Nos. 25, 26 and 27 containing other discoloration inhibitors together with the microbicide already discolored to liver brown before the weathering test. On the other hand, the test product Nos. 24 and 29 containing potassium salt of methylbenzotriazole together with the microbicide did not substantially show discoloration not only before the weathering test, but also after the weathering test.

TABLE 12

| Test product | Before weathering test | | | After weathering test | | | Color differ- |
|---|---|---|---|---|---|---|---|
| No. | L | a | b | L | a | b | ence ΔE |
| 30 | 94.9 | −0.8 | 4.2 | 94.8 | −0.7 | 5.2 | 1.0 |
| 31 | 75.3 | 2.5 | 6.1 | 58.7 | 0.8 | 3.6 | 16.9 |
| 32 | 93.6 | −1.4 | 6.2 | 92.0 | −1.4 | 8.1 | 2.5 |
| 33 | 77.7 | 2.3 | 7.2 | 57.2 | 0.8 | 3.8 | 20.8 |
| 34 | 79.6 | 2.2 | 6.6 | 64.0 | 1.7 | 5.7 | 15.6 |

TABLE 12-continued

| Test product | Before weathering test | | | After weathering test | | | Color differ- |
|---|---|---|---|---|---|---|---|
| No. | L | a | b | L | a | b | ence ΔE |
| 35 | 80.2 | 1.8 | 6.6 | 61.2 | 1.1 | 4.7 | 19.1 |
| 36 | 93.9 | −1.3 | 5.7 | 92.7 | −1.3 | 7.6 | 2.2 |
| 37 | 64.4 | 4.2 | 2.4 | 42.9 | 1.1 | 1.8 | 21.7 |
| 38 | 93.9 | −1.2 | 5.7 | 90.2 | −0.7 | 86. | 4.7 |

As can be seen from Table 12, as compared with the test product No. 30 containing only the sealing base and containing neither the microbicide nor the discoloration inhibitor, the test product Nos. 31 and 37 containing only the microbicide and containing no discoloration inhibitor in addition to the sealing base and the test product Nos. 33–35 containing the microbicide and the conventional discoloration inhibitors already discolored to liver brown before the weathering test. On the other hand, the test product Nos. 32, 36 and 38 containing potassium salt of methylbenzotriazole or this and the conventional discoloration inhibitor together with the microbicide showed substantially no discoloration before the weathering test.

It can be seen that the test product Nos. 31 and 37 containing no discoloration inhibitor and the test product Nos. 33–35 containing the conventional discoloration inhibitors had large ΔE which shows color difference before and after the weathering test and were inferior in weathering resistance, while the test product Nos. 32, 36 and 38 containing potassium salt of methylbenzotriazole as the discoloration inhibitor had small ΔE before and after the weathering test and were superior in weathering resistance.

Evaluation Test 4

[Antifungal Activity Test]

The sample Nos. 22, 23 and 24 obtained in Example 4 were subjected to the following antifungal activity test.

Each of the sealing compositions was filled in a mold of 5 cm×5 cm×0.5 cm, air-dried for one day and then removed from the mold. This was used as a test piece. Cladosporium cladosporioides was used as a test fungus. The test piece was immersed in a spore suspension of the test fungus and was placed on a potato dextrose agar medium and left to stand at 25° C. and 95%RH for 28 days. Deep green fungi grew on the whole surface of the test piece No. 22, but no fungi grew on the test piece Nos. 23 and 24.

The same antifungal activity test was conducted on the test piece Nos. 25–29 and no fungi grew on all of these test pieces containing the microbicide.

Evaluation Test 5

[Antimicrobial Activity Test]

The sample Nos. 30–38 obtained in Example 5 were subjected to the same antimicrobial activity test as the evaluation test 2. The results are shown in Table 13.

TABLE 13

| Sample No. | The number of bacteria |
|---|---|
| 30 | $2.4 \times 10^3$ |
| 31 | 0 |
| 32 | 0 |
| 33 | 0 |
| 34 | 0 |
| 35 | 0 |
| 36 | 0 |
| 37 | 0 |
| 38 | 0 |

As can be seen from Table 13, sample Nos. 31–38 containing the microbicide all showed excellent antimicrobial activity.

What is claimed is:

1. An antimicrobial composition which contains an inorganic compound on which silver ion is supported and a compound represented by the following formula (2):

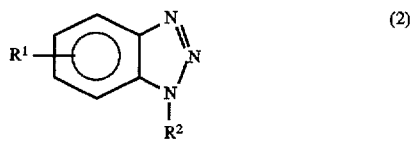

wherein $R^1$ is hydrogen or methyl and $R^2$ is hydrogen, or an alkali metal salt thereof, wherein the inorganic compound on which silver ion is supported is represented by the following formula (1):

$$Ag_a M^1{}_b M^2{}_2 (PO_4)_3 \cdot nH_2O \tag{1}$$

wherein $M^1$ is at least one ion selected from alkali metal ion, alkaline earth metal ion, ammonium ion and hydrogen ion, $M^2$ is a tetravalent metal, n is a number which satisfies $0 \leq n \leq 6$, and a and b are positive numbers which satisfy $a+mb=1$ where m is a valence of $M^1$.

2. An antimicrobial composition according to claim 1, wherein the compound represented by the formula [2] is methylbenzotriazole or the potassium salt thereof.

3. An antimicrobial composition according to claim 1, wherein the compound represented by the formula [2] is contained in an amount of 0.1 to 100 parts by weight based on 100 parts by weight of the inorganic compound on which silver ion is supported.

4. In a flowable composition which is hardenable to a rigid form, comprising a base material which is hardenable to a rigid form, an inorganic microbicide comprising silver ion, and a benzotriazole discoloration inhibitor, the improvement wherein the inorganic microbicide comprising silver ion is represented by the following formula (1):

$$Ag_a M^1{}_b M^2{}_2 (PO_4)_3 \cdot nH_2O \tag{1}$$

wherein $M^1$ is at least one ion selected from alkali metal ion, alkaline earth metal ion, ammonium ion and hydrogen ion, $M^2$ is a tetravalent metal, n is a number which satisfies $0 \leq n \leq 6$, and a and b are positive numbers which satisfy $a+mb=1$ where m is a valence of $M^1$, and wherein said benzotriazole discoloration inhibitor is a compound of the formula (2):

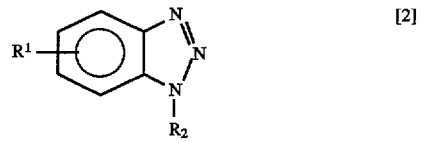

wherein $R^1$ is hydrogen or methyl and $R^2$ is hydrogen, or an alkali metal salt thereof, said microbicide being present in the range of 0.05 to 50 parts by weight per 100 parts by weight of said base material, and said discoloration inhibitor being present in an amount of 0.1 to 100 parts by weight based on 100 parts by weight of said microbicide.

5. A composition in accordance with claim 4 in the form of a paint.

6. A composition in accordance with claim 4 in the form of a sealant.

7. A composition according to claim 4 wherein said base material is an inorganic cement.

8. A composition according to claim 7 wherein said cement is a mortar.

9. A composition according to claim 4 wherein said base material is a resin.

* * * * *